(12) United States Patent
Giri et al.

(10) Patent No.: US 11,375,914 B2
(45) Date of Patent: Jul. 5, 2022

(54) DATA ACQUISITION ACCELERATION IN MAGNETIC RESONANCE ANGIOGRAPHY APPLICATIONS USING MAGNETIZATION-PREPARED SIMULTANEOUS MULTI-SLICE ACQUISITION

(71) Applicants: Siemens Healthcare GmbH, Erlangen (DE); NorthShore University HealthSystem, Evanston, IL (US)

(72) Inventors: Shivraman Giri, Cambridge, MA (US); Robert R. Edelman, Highland Park, IL (US); Ioannis Koktzoglou, Des Plaines, IL (US); Himanshu Bhat, Newton, MA (US)

(73) Assignees: Siemens Healthcare GmbH, Erlangen (DE); NorthShore University Healthsystem, Evanston, IL (US)

( * ) Notice: Subject to any disclaimer, the term of this patent is extended or adjusted under 35 U.S.C. 154(b) by 435 days.

(21) Appl. No.: 16/687,733

(22) Filed: Nov. 19, 2019

(65) Prior Publication Data
US 2020/0085322 A1    Mar. 19, 2020

Related U.S. Application Data

(62) Division of application No. 15/332,107, filed on Oct. 24, 2016, now Pat. No. 10,517,490.

(51) Int. Cl.
*A61B 5/026* (2006.01)
*G01R 33/563* (2006.01)
(Continued)

(52) U.S. Cl.
CPC ........ *A61B 5/0263* (2013.01); *G01R 33/5607* (2013.01); *G01R 33/5635* (2013.01); *A61B 5/7285* (2013.01); *G01R 33/4835* (2013.01)

(58) Field of Classification Search
CPC ........... G01R 33/4833; G01R 33/5635; G01R 33/561; G01R 33/4835; G01R 33/563;
(Continued)

(56) References Cited

U.S. PATENT DOCUMENTS 8,332,010 B2    12/2012  Edelman
2007/0265522 A1*  11/2007  Kassai ............... G01R 33/5673
                                                            600/411
(Continued)

OTHER PUBLICATIONS

Edelman, Robert R., et al. "Quiescent-Interval Single-Shot Unenhanced Magnetic Resonance Angiography of Peripheral Vascular Disease: Technical Considerations and Clinical Feasibility." Magnetic resonance in medicine 63.4 (2010): 951-958.
(Continued)

*Primary Examiner* — Amelie R Davis
*Assistant Examiner* — Helene Bor

(57) ABSTRACT

A method for producing an image representative of the vasculature of a subject using a MRI system includes the acquisition of a signal indicative of a subject' cardiac phase. During each heartbeat of the subject, image slices of a volume covering a region of interest (ROI) within the subject are acquired by applying a volume-selective venous suppression pulse to suppress (a) venous signal for an upper slice in the ROI; (b) venous signal for slices that are upstream for venous flow in the ROI; and (c) background signal from the upstream slices. Next, a slice-selective background suppression pulse is applied to suppress background signal of the upper slice. Following a quiescent time interval, a spectrally selective fat suppression pulse is applied to the entire volume to attenuate signal from background fat signal. Then, a simultaneous multi-slice acquisition of the upper slice and the upstream slices is performed.

10 Claims, 7 Drawing Sheets

(51) Int. Cl.
  *G01R 33/56* (2006.01)
  *G01R 33/483* (2006.01)
  *A61B 5/00* (2006.01)

(58) Field of Classification Search
  CPC ........ G01R 33/56308; G01R 33/56316; G01R 33/5607; A61B 5/0263; A61B 5/7285; A61B 5/055
  See application file for complete search history.

(56) References Cited

U.S. PATENT DOCUMENTS

| | | | |
|---|---|---|---|
| 2010/0268062 A1* | 10/2010 | Edelman | A61B 5/7285 600/410 |
| 2014/0200435 A1* | 7/2014 | Edelman | G01R 33/56509 600/410 |

OTHER PUBLICATIONS

Breuer, Felix A., et al. "Controlled Aliasing in Parallel Imaging Results in Higher Acceleration (CAIPIRINHA) for Multi-Slice Imaging." Magnetic resonance in medicine 53.3 (2005): 684-691.

\* cited by examiner

DATA ACQUISITION ACCELERATION IN MAGNETIC RESONANCE ANGIOGRAPHY APPLICATIONS USING MAGNETIZATION-PREPARED SIMULTANEOUS MULTI-SLICE ACQUISITION

CROSS REFERENCE TO RELATED APPLICATIONS

This is a divisional application of U.S. Ser. No. 15/332,107 filed on Oct. 24, 2016, the contents of which are incorporated by reference.

TECHNOLOGY FIELD

The present invention relates generally to methods, systems, and apparatuses for accelerating data acquisition in magnetic resonance angiography applications using magnetization-prepared simultaneous multi-slice acquisition.

BACKGROUND

Non contrast-enhanced magnetic resonance angiography (NE-MRA) is useful in the evaluation of vascular pathologies, especially in patients with impaired renal function. Most of the NE-MRA techniques rely on blood flow into a sequential series of 20 slices or 30 blocks until the entire vascular territory of interest is imaged. This process of sequential acquisition can potentially result in long scan times for the patient.

Many techniques exist to accelerate image acquisition to thereby reduce patient examination time. These exploit different aspects inherent in MR data. For instance, the use of phased-array coils provides additional information encoded in spatially varying sensitivity of the individual coil elements; this can be used to extract more information from the same data. More advanced techniques have been developed that simultaneously excite multiple spatially-separated slices, and then use coil sensitivities to extract the information in each individual slice; these are collectively called simultaneous multi-slice (SMS) imaging.

In addition to maximizing the signal from blood vessels, NE-MRA requires the minimization of signal from other tissues (e.g., background muscles, fat, etc.) so as to improve conspicuity of vessels. Often, radiofrequency suppression pulses are used for this purpose; these pulses suppress the magnetization from the background tissues, thus minimizing the signal emanating from them.

As mentioned above, conventional NE-MRA techniques rely on inflow of blood to generate the required contrast—accentuation of arteries and suppression of veins and background. One such NE-MRA technique is called quiescent interval slice-selective (QISS). In this approach, three different preparation pulses are used to suppress background tissue, venous signal, and fat signal. Quiescent interval (QI) is a time interval during which no activity takes place so as to permit inflow of sufficient unsuppressed blood into the slice of interest. The MR signal acquired after the QI time represents primarily arterial signal. The process is then repeated for all slices, until the entire vascular anatomy of interest is covered. The series of slices are then stacked together to depict the vascular tree.

The use of SMS is attractive for accelerating data acquisition of NE-MRA techniques such as QISS; however, it requires redesign of spatial and temporal application of magnetization preparation pulses to accomplish similar images in less time. Thus, it is desired to provide techniques for combining NE-MRA with SMS and magnetization preparation pulses in a manner that minimizes the overall acquisition time.

SUMMARY

Embodiments of the present invention address and overcome one or more of the above shortcomings and drawbacks, by providing methods, systems, and apparatuses which accelerate data acquisition in magnetic resonance applications using magnetization prepared simultaneous multi-slice acquisition. Briefly, the techniques described herein combine NE-MRA with SMS using suppression pulses that are modified such that the venous suppression pulse not only suppresses the venous signal for each acquired slice, but the background for the slice that is upstream for venous flow is also suppressed.

According to some embodiments, a method for using magnetic resonance angiography to produce an image representative of the vasculature of a subject with a magnetic resonance imaging (MRI) system includes acquiring a signal indicative of a cardiac phase of the subject. During each heartbeat of the subject (e.g., following a user-selected time delay after the R-wave of each heartbeat), image slices of a volume covering a region of interest within the subject are acquired using an acquisition process. During this process, a volume-selective venous suppression pulse is applied to suppress (a) venous signal for an upper slice in the region of interest; (b) venous signal for one or more slices that are upstream for venous flow in the region of interest; and (c) background signal from the upstream slices. The volume-selective venous suppression pulse may include, for example, a tracking saturation pulse applied downstream to the upper slice and the upstream slices. Next, a slice-selective background suppression pulse is applied to suppress background signal of the upper slice. The slice-selective background suppression pulse may apply, for example, a 90 degree or 180 degree flip angle to the upper slice. Following a quiescent time interval, a spectrally selective fat suppression pulse is applied to the entire volume to attenuate signal from background fat signal. Once the preparation pulses have been applied, a simultaneous multi-slice acquisition of the upper slice and the upstream slices is performed. This simultaneous multi-slice acquisition may be performed using a single-shot pulse sequence. For example, in some embodiments, the single-shot pulse sequence is a balanced steady-state free precession pulse sequence or spoiled gradient echo pulse sequence.

In some embodiments of the aforementioned method, the spectrally selective fat suppression pulse is a 90 degree RF pulse which rotates magnetizations in fat tissue of the entire volume into the x-y plane of the subject. In other embodiments, the spectrally selective fat suppression pulse is a 180 degree RF pulse which completely inverts longitudinal magnetization of fat in the entire volume. The method may then further include waiting a predetermined inversion time prior to performing the simultaneous multi-slice acquisition of the upper slice and the one or more upstream slices. This predetermined inversion time may be selected such that longitudinal magnetization of fat in the upper slice and the upstream slices recovers through a zero point when acquiring k-space data during the simultaneous multi-slice acquisition.

According to other embodiments, a second method for using magnetic resonance angiography to produce an image representative of the vasculature of a subject with a MRI system includes acquiring a signal indicative of a cardiac phase of the subject. During each heartbeat of the subject, image slices of a volume covering a region of interest within the subject are acquired using an acquisition process. During this process, for each of the plurality of image slices, the following pulses are applied: (a) a volume-selective venous suppression pulse to suppress venous signal downstream from venous flow into the image slice and (b) a slice-selective background suppression pulse to suppress background signal of the image slice. Additionally, following a quiescent time interval, a spectrally selective fat suppression pulse is applied to attenuate signal from background fat signal in the entire volume. Then, a simultaneous multi-slice acquisition of the plurality of image slices may be performed. Various features, enhancements, and other modifications may be made to this second method which are similar to those described above with respect to the other method for using magnetic resonance angiography to produce an image representative of the vasculature of a subject discussed above.

According to another aspect of the present invention, a system for using magnetic resonance angiography to produce an image representative of the vasculature of a subject includes an electrocardiogram device, an imaging device, and a central control computer. The electrocardiogram device is configured to acquire a signal indicative of a cardiac phase of the subject. The imaging device includes a plurality of coils which are used to apply a preparation pulse sequence to a volume during each heartbeat of the subject. This preparation pulse sequence comprises a volume-selective venous suppression pulse that suppresses (a) venous signal from an upper slice in a region of interest, (b) venous signal from one or more upstream slices that are upstream for venous flow in the region of interest, and (c) background signal from the one or more upstream slices. The sequence further includes a slice-selective background suppression pulse that suppresses background signal of the upper slice, and a spectrally selective fat suppression pulse applied to the volume to attenuate signal from background fat signal. The imaging device is further configured to perform a simultaneous multi-slice acquisition of the upper slice and the one or more upstream slices following each preparation pulse sequence to update a k-space dataset covering the region of interest. The central control computer unit is configured to apply a reconstruction process to the k-space dataset to generate one or more images.

Additional features and advantages of the invention will be made apparent from the following detailed description of illustrative embodiments that proceeds with reference to the accompanying drawings.

BRIEF DESCRIPTION OF THE DRAWINGS

The foregoing and other aspects of the present invention are best understood from the following detailed description when read in connection with the accompanying drawings. For the purpose of illustrating the invention, there is shown in the drawings embodiments that are presently preferred, it being understood, however, that the invention is not limited to the specific instrumentalities disclosed. Included in the drawings are the following Figures.

DETAILED DESCRIPTION OF ILLUSTRATIVE EMBODIMENTS

The following disclosure describes the present invention according to several embodiments directed at methods, systems, and apparatuses related to accelerating data acquisition in magnetic resonance angiography applications. More specifically, the techniques described herein combine SMS imaging with magnetization preparation to achieve scan time reduction in magnetic resonance angiography (MRA) applications by a factor of N, where N is the number of slices that are excited simultaneously. As described in more detail below, this is achieved, in part, by using a preparatory pulse sequence comprising a venous suppression pulse that not only suppresses the venous signal for each acquired slice, but also the background for the slice that is upstream for venous flow.

Figure 1:
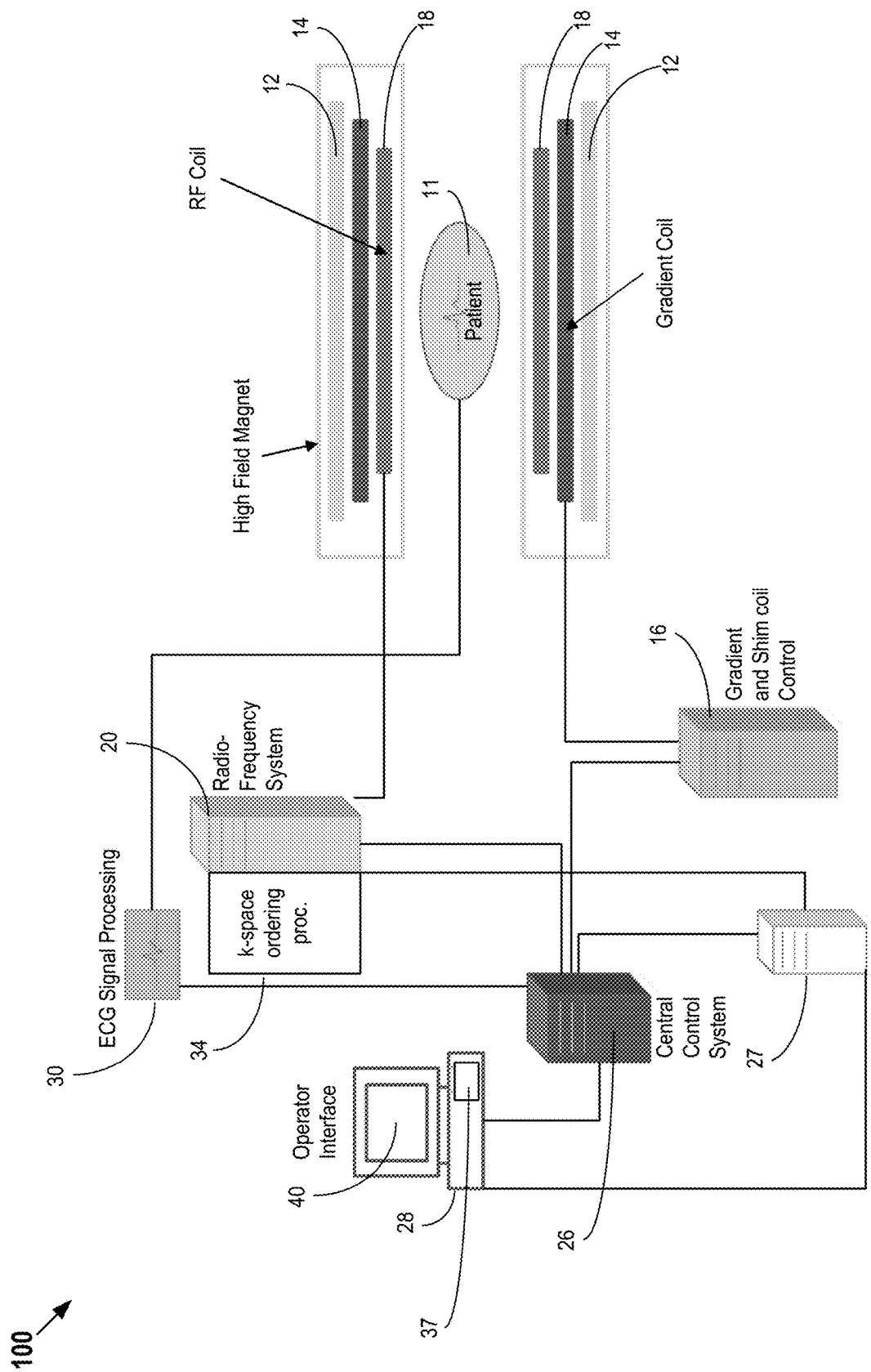
FIG. 1 shows a system for ordering acquisition of frequency domain components representing magnetic resonance imaging (MRI) data for storage in a k-space storage array, as used by some embodiments of the present invention.

FIG. 1 shows a system 100 for ordering acquisition of frequency domain components representing magnetic resonance imaging (MRI) data for storage in a k-space storage array, as used by some embodiments of the present invention. In system 100, magnetic coils 12 create a static base magnetic field in the body of patient 11 to be imaged and positioned on a table. Within the magnet system are gradient coils 14 for producing position dependent magnetic field gradients superimposed on the static magnetic field. Gradient coils 14, in response to gradient signals supplied thereto by a gradient and shim coil control module 16, produce position dependent and shimmed magnetic field gradients in three orthogonal directions and generates magnetic field pulse sequences. The shimmed gradients compensate for inhomogeneity and variability in an MRI device magnetic field resulting from patient anatomical variation and other sources. The magnetic field gradients include a slice-selection gradient magnetic field, a phase-encoding gradient magnetic field and a readout gradient magnetic field that are applied to patient 11.

Further radio frequency (RF) module 20 provides RF pulse signals to RF coil 18, which in response produces magnetic field pulses which rotate the spins of the protons in the imaged body of the patient 11 by ninety degrees or by one hundred and eighty degrees for so-called "spin echo" imaging, or by angles less than or equal to 90 degrees for so-called "gradient echo" imaging. Gradient and shim coil control module 16 in conjunction with RF module 20, as directed by central control unit 26, control slice-selection, phase-encoding, readout gradient magnetic fields, radio frequency transmission, and magnetic resonance signal detection, to acquire magnetic resonance signals representing planar slices of patient 11.

In response to applied RF pulse signals, the RF coil 18 receives magnetic resonance signals, i.e., signals from the excited protons within the body as they return to an equilibrium position established by the static and gradient magnetic fields. The magnetic resonance signals are detected and processed by a detector within RF module 20 and k-space component processor unit 34 to provide a magnetic resonance dataset to an image data processor for processing into an image. In some embodiments, the image data processor is located in central control unit 26. However, in other embodiments such as the one depicted in FIG. 1, the image data processor is located in a separate unit 27. Electrocardiogram (ECG) synchronization signal generator 30 provides ECG signals used for pulse sequence and imaging synchronization. A two or three dimensional k-space storage array of individual data elements in k-space component processor unit 34 stores corresponding individual frequency components comprising a magnetic resonance dataset. The k-space array of individual data elements has a designated center and individual data elements individually have a radius to the designated center.

A magnetic field generator (comprising coils 12, 14, and 18) generates a magnetic field for use in acquiring multiple individual frequency components corresponding to individual data elements in the storage array. The individual frequency components are successively acquired in an order in which radius of respective corresponding individual data elements increases and decreases along a substantially spiral path as the multiple individual frequency components are sequentially acquired during acquisition of a magnetic resonance dataset representing a magnetic resonance image. A storage processor in the k-space component processor unit 34 stores individual frequency components acquired using the magnetic field in corresponding individual data elements in the array. The radius of respective corresponding individual data elements alternately increases and decreases as multiple sequential individual frequency components are acquired. The magnetic field acquires individual frequency components in an order corresponding to a sequence of substantially adjacent individual data elements in the array and magnetic field gradient change between successively acquired frequency components which are substantially minimized.

Central control unit 26 uses information stored in an internal database to process the detected magnetic resonance signals in a coordinated manner to generate high quality images of a selected slice(s) of the body (e.g., using the image data processor) and adjusts other parameters of system 100. The stored information comprises predetermined pulse sequence and magnetic field gradient and strength data as well as data indicating timing, orientation and spatial volume of gradient magnetic fields to be applied in imaging. Generated images are presented on display 40 of the operator interface. Computer 28 of the operator interface includes a graphical user interface (GUI) enabling user interaction with central control unit 26 and enables user modification of magnetic resonance imaging signals in substantially real time. Continuing with reference to FIG. 1, display processor 37 processes the magnetic resonance signals to reconstruct one or more images for presentation on display 40, for example. Various techniques generally known in the art may be used for reconstruction.

Figure 2A:
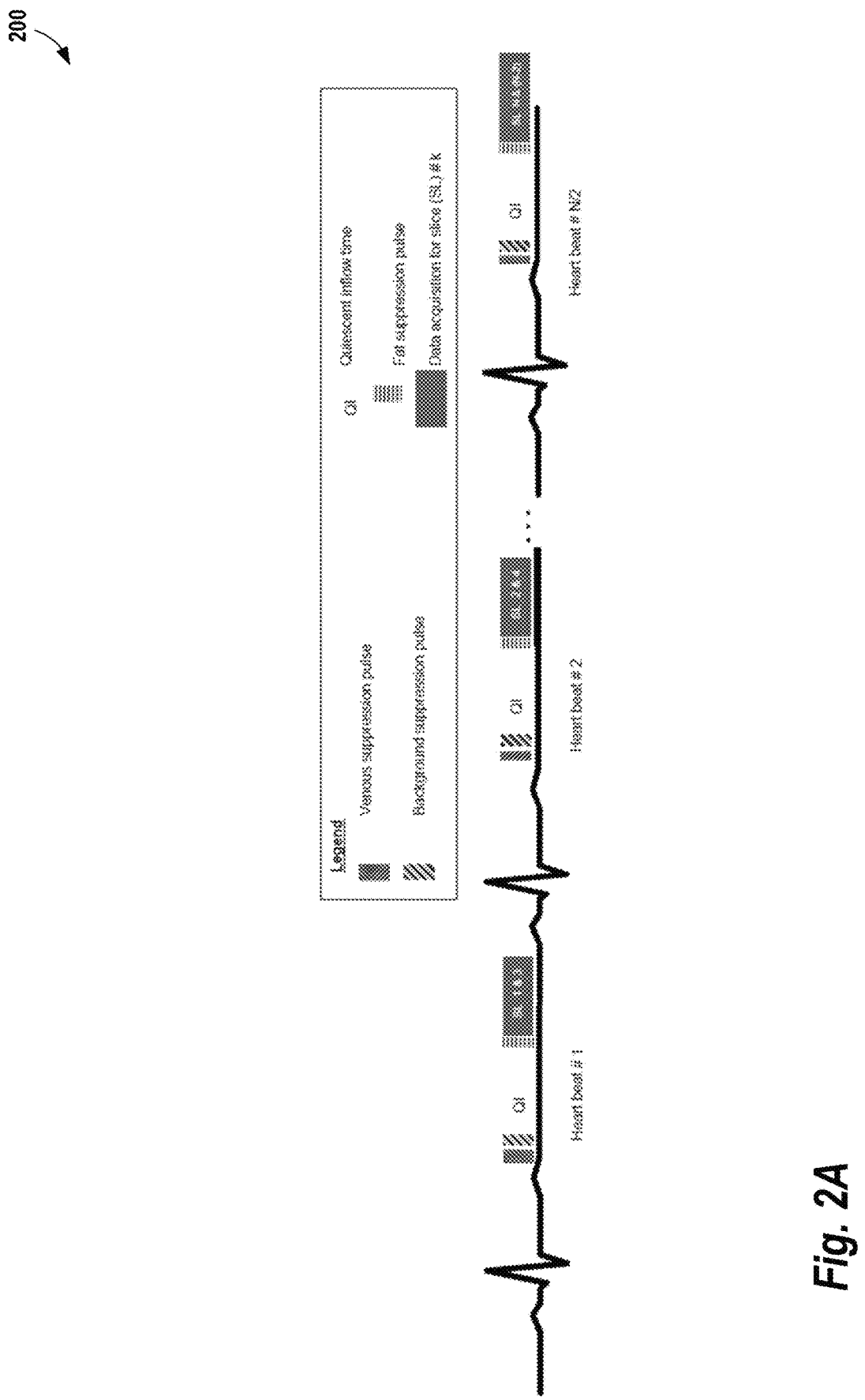
FIG. 2A provides an illustration of an image acquisition sequence 200 that may be implemented on the system 100, according to some of the techniques described herein.
Figure 2B:
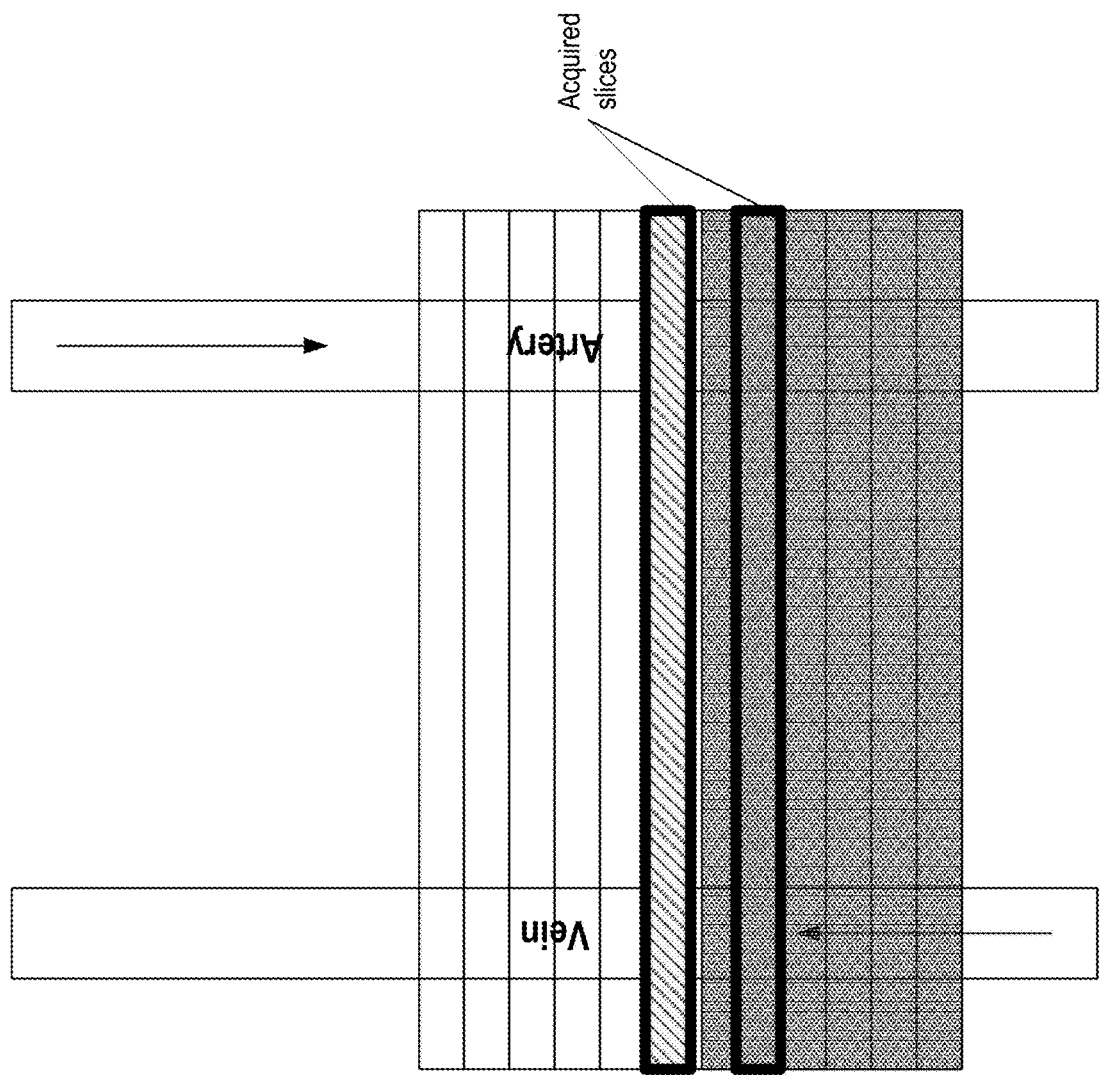
FIG. 2B shows the spatial location of the pulses shown in FIG. 2A in a schematic of vascular anatomy.

FIG. 2A provides an illustration of an image acquisition sequence 200 that may be implemented on the system 100, according to some of the techniques described herein. Briefly, in each heart-beat, multiple slices are being acquired. The suppression pulses are modified such that the venous suppression pulse not only suppresses the venous signal for both slices, but also the background for the slice that is upstream for venous flow. FIG. 2B shows the spatial location of those pulses in a schematic of vascular anatomy. A vein and artery are shown in FIG. 2B, with arrows indicating the direction of blood flow. The slices of interest are shown by bold-lined boxes. The result of venous and background suppression pulses are indicated as per the legend in FIG. 2A.

The example of FIG. 2A shows an implementation for N=2 (i.e. simultaneously acquiring 2 slices). The slices being simultaneously imaged should be spatially as close together as permitted by the design of pulses so as to allow adequate arterial inflow to all slices within the same heartbeat.

The preparation pulses are modified such that the venous suppression pulse is used to suppress venous signal for both slices and also the background of the slice that is upstream for venous flow. To suppress the background of the other slice, a slice-selective saturation RF pulse is applied to the slice to set the longitudinal magnetization of tissues within the slice to zero is used. The pulse may rotate the magnetization by a 90° flip angle or a 180° flip angle, although use of a 180° flip angle may provide more sensitivity to variations in heart rate compared with a 90° flip angle.

During the QI time, blood that was unaffected by the two suppression pulses now flows into both slices. A spectrally selective fat-suppression pulse is applied to attenuate signal from background fat signal. This is followed by the SMS acquisition. The process is then repeated in each heartbeat, acquiring multiple slices in each heart-beat as against a single slice per heart-beat as is done in conventional approaches.

Figure 3A:
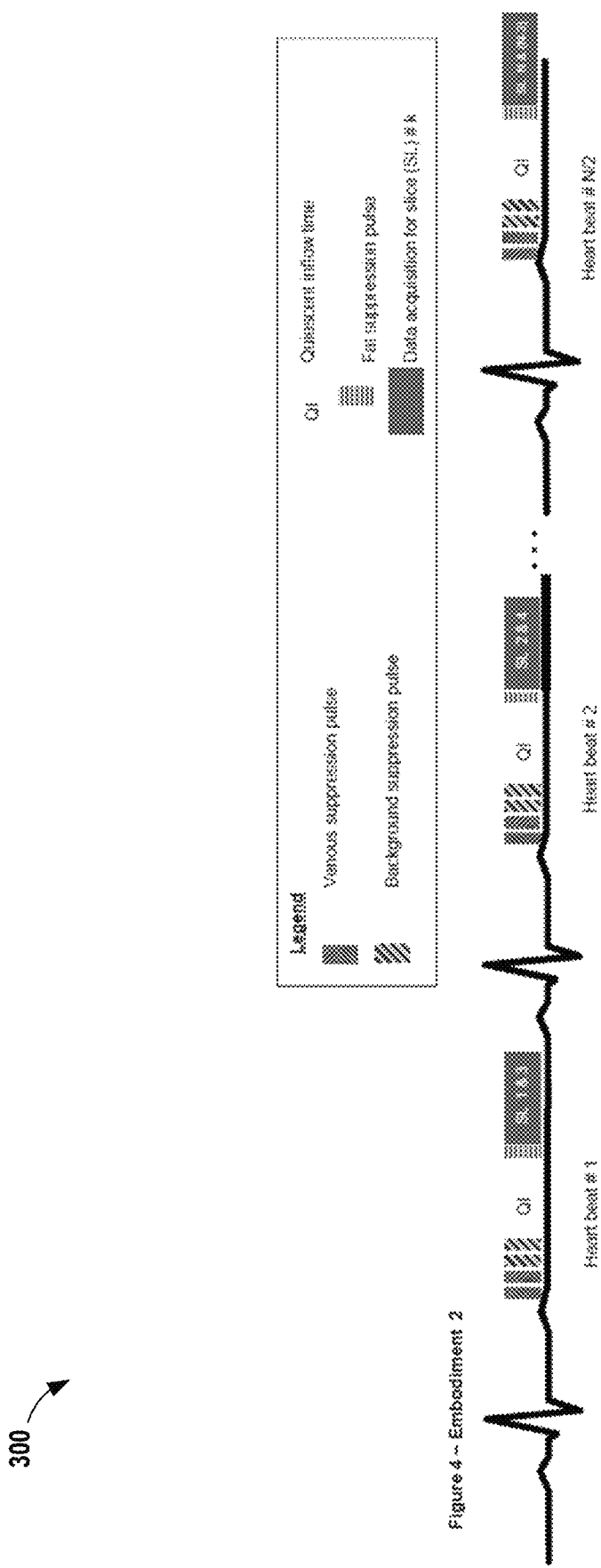
FIG. 3A provides an illustration of an alternative image acquisition sequence 300, according to some embodiments.

FIG. 3A provides an illustration of an alternative image acquisition sequence 300, according to some embodiments. As with implementation shown in FIG. 2, during the image acquisition sequence 300, multiple slices are acquired in each heart-beat. However, each slice has its dedicated set of two suppression pulses for background and venous suppression. The second venous suppression pulse is applied to suppress venous blood between slices. The venous suppression pulse of the slice that is upstream for arterial flow (and downstream for venous flow) is very thin, covering only the gap between the two slices. Thus, a total of 4 suppression pulses are applied, giving more flexibility in their design and spatial selectivity, at the expense of transmitting additional radiofrequency energy which is deposited into the body being imaged.

Figure 3B:
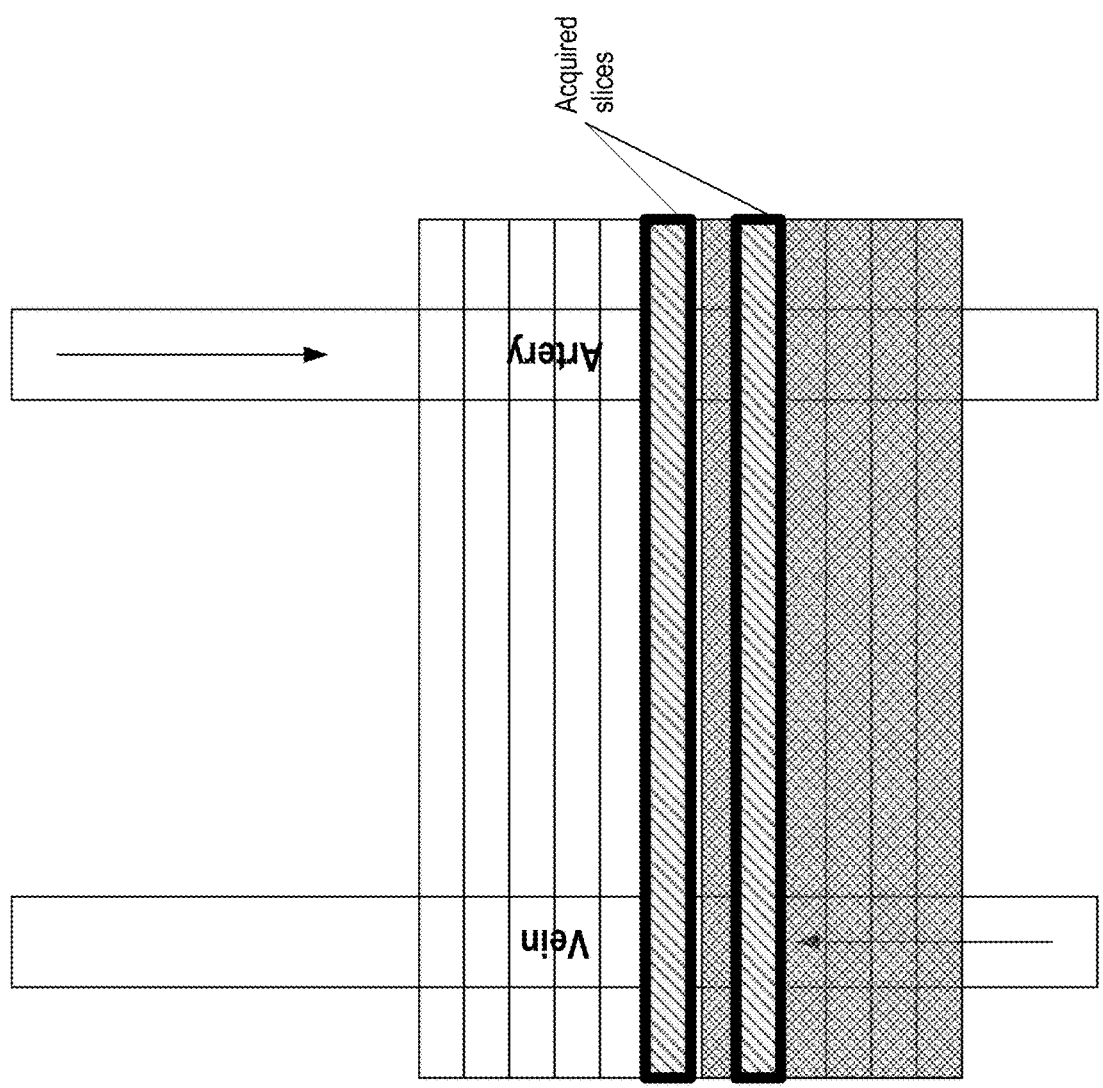
FIG. 3B shows the spatial location of the pulses shown in FIG. 3A in a schematic of vascular anatomy.

FIG. 3B shows the spatial location of the pulses applied in FIG. 3A in a schematic of vascular anatomy. As with the example provided in FIG. 2B, a vein and artery, with arrows indicating the direction of blood flow. The slices of interest are shown by bold-lined boxes. The result of venous and background suppression pulses are indicated as per the legend in FIG. 3A.

Figure 4:
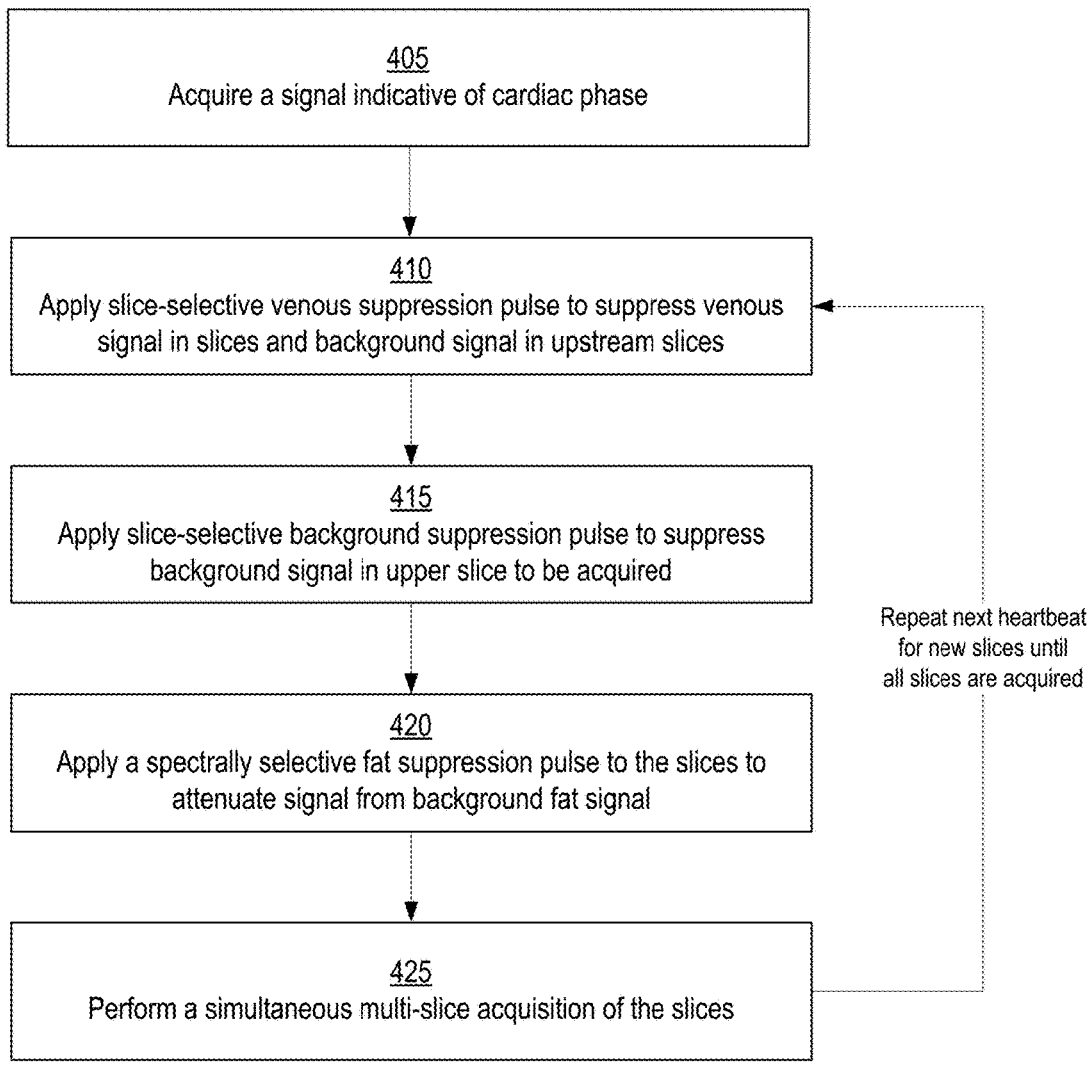
FIG. 4 shows a process 400 for using magnetic resonance angiography to produce an image representative of the vasculature of a subject, according to some embodiments of the present invention.

FIG. 4 shows a process 400 for using magnetic resonance angiography to produce an image representative of the vasculature of a subject, according to some embodiments of the present invention. Starting at step 405 a signal indicative of a cardiac phase of the subject is acquired, for example, using an ECG device operably coupled to the MRI system. Next, at steps 410-425, an acquisition process is performed during each heartbeat of the subject to acquire a plurality of image slices covering a region of interest within the subject. Briefly, the acquisition process includes a sequence of preparatory pulses applied at 410-420 to a group of slices followed by a simultaneous multi-slice (SMS) acquisition of the prepared slices at step 425.

Each acquisition process may be performed following a user-selected time delay after the R-wave of each heartbeat. The slices acquired during each heartbeat include an "upper" slice which is the top-most slice to be acquired and one or more slices that are upstream for venous flow in the region of interest. At step 410, a volume-selective venous suppression pulse is applied to the subject to suppress (a) venous signal from an upper slice in the region of interest; (b) venous signal from the upstream slices; and (c) background signal from the upstream slices. This volume-selective venous suppression pulse may be, for example, a tracking saturation pulse applied downstream to the upper slice and the upstream slices.

At step 415, a slice-selective background suppression pulse is applied to the subject to suppress background signal of the upper slice. The slice-selective background suppression pulse may apply, for example, a 90 or 180 degree flip angle to the upper slice. Following a quiescent time interval, a spectrally selective fat suppression pulse is applied at step 420 to the upper slice and the upstream slices to attenuate signal from background fat signal. In some embodiments, the spectrally selective fat suppression pulse is a 90° RF pulse which rotates magnetizations of the upper slice and the one or more upstream slices into the x-y plane of the subject. In other embodiments, the spectrally selective fat suppression pulse is a 180° RF pulse which completely inverts longitudinal magnetization of fat in the slices. The method 400 may then further include an additional step (not shown in FIG. 4) a delay is introduced to wait a predetermined inversion time prior to performing the SMS acquisition of the slices. This predetermined inversion time is selected such that longitudinal magnetization of fat in the slices recovers through a zero point when acquiring k-space data during the acquisition.

Continuing with reference to FIG. 4, at step 425, a SMS is performed to acquire k-space data covering the upper slice and the upstream slices. This acquisition may generally be performed using any technique known in the art. For example, in some embodiments, single-shot imaging techniques are applied at step 425. Various pulse sequences known in the art may be used in performing the acquisition. For example, in one embodiment, a balanced steady-state free precession pulse sequence is used at step 425.

Figure 5:
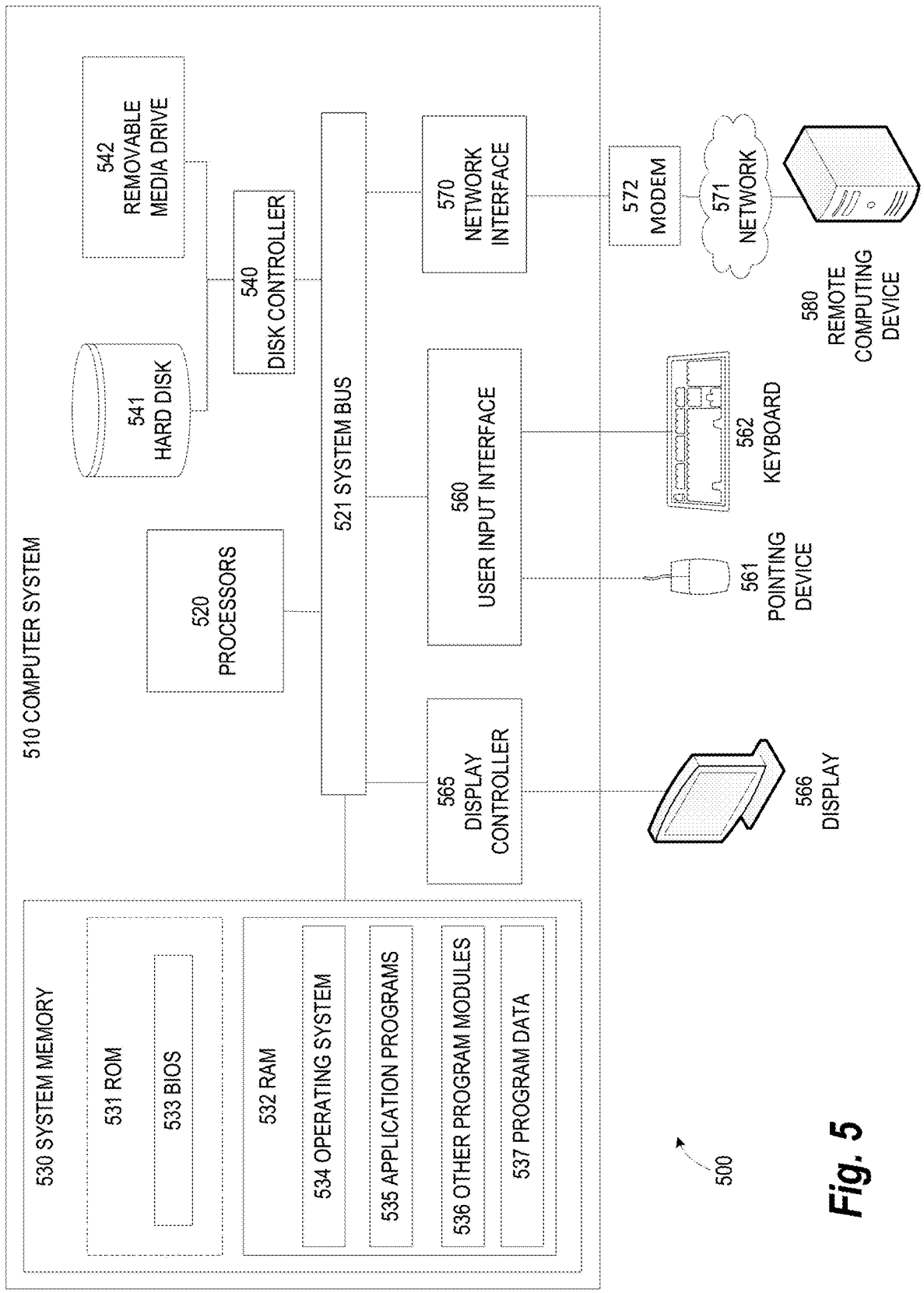
FIG. 5 illustrates an exemplary computing environment 500 within which embodiments of the invention may be implemented.

FIG. 5 illustrates an exemplary computing environment 500 within which embodiments of the invention may be implemented. For example, this computing environment 500 may be used to implement portions of the process 400 described above with respect to FIG. 4. In some embodiments, the computing environment 500 may be used to implement one or more of the components illustrated in the system 100 of FIG. 1. The computing environment 500 may include computer system 510, which is one example of a computing system upon which embodiments of the invention may be implemented. Computers and computing environments, such as computer system 510 and computing environment 500, are known to those of skill in the art and thus are described briefly here.

As shown in FIG. 5, the computer system 510 may include a communication mechanism such as a bus 521 or other communication mechanism for communicating information within the computer system 510. The computer system 510 further includes one or more processors 520 coupled with the bus 521 for processing the information. The processors 520 may include one or more central processing units (CPUs), graphical processing units (GPUs), or any other processor known in the art.

The computer system 510 also includes a system memory 530 coupled to the bus 521 for storing information and instructions to be executed by processors 520. The system memory 530 may include computer readable storage media in the form of volatile and/or nonvolatile memory, such as read only memory (ROM) 531 and/or random access memory (RAM) 532. The system memory RAM 532 may include other dynamic storage device(s) (e.g., dynamic RAM, static RAM, and synchronous DRAM). The system memory ROM 531 may include other static storage device(s) (e.g., programmable ROM, erasable PROM, and electrically erasable PROM). In addition, the system memory 530 may be used for storing temporary variables or other intermediate information during the execution of instructions by the processors 520. A basic input/output system (BIOS) 533 containing the basic routines that help to transfer information between elements within computer system 510, such as during start-up, may be stored in ROM 531. RAM 532 may contain data and/or program modules that are immediately accessible to and/or presently being operated on by the processors 520. System memory 530 may additionally include, for example, operating system 534, application programs 535, other program modules 536 and program data 537.

The computer system 510 also includes a disk controller 540 coupled to the bus 521 to control one or more storage devices for storing information and instructions, such as a hard disk 541 and a removable media drive 542 (e.g., floppy disk drive, compact disc drive, tape drive, and/or solid state drive). The storage devices may be added to the computer system 510 using an appropriate device interface (e.g., a small computer system interface (SCSI), integrated device electronics (IDE), Universal Serial Bus (USB), or FireWire).

The computer system 510 may also include a display controller 565 coupled to the bus 521 to control a display 566, such as a cathode ray tube (CRT) or liquid crystal display (LCD), for displaying information to a computer user. The computer system includes an input interface 560 and one or more input devices, such as a keyboard 562 and a pointing device 561, for interacting with a computer user and providing information to the processor 520. The pointing device 561, for example, may be a mouse, a trackball, or a pointing stick for communicating direction information and command selections to the processor 520 and for controlling cursor movement on the display 566. The display 566 may provide a touch screen interface which allows input to supplement or replace the communication of direction information and command selections by the pointing device 561.

The computer system 510 may perform a portion or all of the processing steps of embodiments of the invention in response to the processors 520 executing one or more sequences of one or more instructions contained in a memory, such as the system memory 530. Such instructions may be read into the system memory 530 from another computer readable medium, such as a hard disk 541 or a removable media drive 542. The hard disk 541 may contain one or more datastores and data files used by embodiments of the present invention. Datastore contents and data files may be encrypted to improve security. The processors 520 may also be employed in a multi-processing arrangement to execute the one or more sequences of instructions contained in system memory 530. In alternative embodiments, hardwired circuitry may be used in place of or in combination with software instructions. Thus, embodiments are not limited to any specific combination of hardware circuitry and software.

As stated above, the computer system 510 may include at least one computer readable medium or memory for holding instructions programmed according to embodiments of the invention and for containing data structures, tables, records, or other data described herein. The term "computer readable medium" as used herein refers to any medium that participates in providing instructions to the processor 520 for execution. A computer readable medium may take many forms including, but not limited to, non-volatile media, volatile media, and transmission media. Non-limiting examples of non-volatile media include optical disks, solid state drives, magnetic disks, and magneto-optical disks, such as hard disk 541 or removable media drive 542. Non-limiting examples of volatile media include dynamic memory, such as system memory 530. Non-limiting examples of transmission media include coaxial cables, copper wire, and fiber optics, including the wires that make up the bus 521. Transmission media may also take the form of acoustic or light waves, such as those generated during radio wave and infrared data communications.

The computing environment 500 may further include the computer system 510 operating in a networked environment using logical connections to one or more remote computers, such as remote computer 580. Remote computer 580 may be a personal computer (laptop or desktop), a mobile device, a server, a router, a network PC, a peer device or other common network node, and typically includes many or all of the elements described above relative to computer system 510. When used in a networking environment, computer system 510 may include modem 572 for establishing communications over a network 571, such as the Internet. Modem 572 may be connected to bus 521 via user network interface 570, or via another appropriate mechanism.

Network 571 may be any network or system generally known in the art, including the Internet, an intranet, a local area network (LAN), a wide area network (WAN), a metropolitan area network (MAN), a direct connection or series of connections, a cellular telephone network, or any other network or medium capable of facilitating communication between computer system 510 and other computers (e.g., remote computer 580). The network 571 may be wired, wireless or a combination thereof. Wired connections may be implemented using Ethernet, Universal Serial Bus (USB), RJ-11 or any other wired connection generally known in the art. Wireless connections may be implemented using Wi-Fi, WiMAX, and Bluetooth, infrared, cellular networks, satellite or any other wireless connection methodology generally known in the art. Additionally, several networks may work alone or in communication with each other to facilitate communication in the network 571.

The embodiments of the present disclosure may be implemented with any combination of hardware and software. In addition, the embodiments of the present disclosure may be included in an article of manufacture (e.g., one or more computer program products) having, for example, computer-readable, non-transitory media. The media has embodied therein, for instance, computer readable program code for providing and facilitating the mechanisms of the embodiments of the present disclosure. The article of manufacture can be included as part of a computer system or sold separately.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

An executable application, as used herein, comprises code or machine readable instructions for conditioning the processor to implement predetermined functions, such as those of an operating system, a context data acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A graphical user interface (GUI), as used herein, comprises one or more display images, generated by a display processor and enabling user interaction with a processor or other device and associated data acquisition and processing functions. The GUI also includes an executable procedure or executable application. The executable procedure or executable application conditions the display processor to generate signals representing the GUI display images. These signals are supplied to a display device which displays the image for viewing by the user. The processor, under control of an executable procedure or executable application, manipulates the GUI display images in response to signals received from the input devices. In this way, the user may interact with the display image using the input devices, enabling user interaction with the processor or other device.

The functions and process steps herein may be performed automatically or wholly or partially in response to user command. An activity (including a step) performed automatically is performed in response to one or more executable instructions or device operation without user direct initiation of the activity.

The system and processes of the figures are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. As described herein, the various systems, subsystems, agents, managers and processes can be implemented using hardware components, software components, and/or combinations thereof. No claim element herein is to be construed under the provisions of 35 U.S.C. 112, sixth paragraph, unless the element is expressly recited using the phrase "means for."

We claim:

1. A method for using magnetic resonance angiography to produce an image representative of the vasculature of a subject with a magnetic resonance imaging (MRI) system, the method comprising:
   acquiring a signal indicative of a cardiac phase of the subject;
   during each heartbeat of the subject, acquiring a plurality of image slices of a volume covering a region of interest within the subject using an acquisition process comprising:
   for each of the plurality of image slices, applying (a) a volume-selective venous suppression pulse to suppress venous signal downstream from venous flow into the image slice and (b) a slice-selective background suppression pulse to suppress background signal of the image slice;

following a quiescent time interval, applying a spectrally selective fat suppression pulse to attenuate signal from background fat signal in the entire volume; and performing a simultaneous multi-slice acquisition of the plurality of image slices.

2. The method of claim 1, wherein each acquisition process is performed following a user-selected time delay after the R-wave of each heartbeat.

3. The method of claim 1, wherein the volume-selective venous suppression pulse comprises a tracking saturation pulse applied downstream from venous flow into the image slice.

4. The method of claim 1, wherein the slice-selective background suppression pulse applies a 90 degree flip angle to the image slice.

5. The method of claim 1, wherein the slice-selective background suppression pulse applies a 180 degree flip angle to the image slice.

6. The method of claim 1, wherein the spectrally selective fat suppression pulse is a 90 degree RF pulse which rotates magnetizations of the plurality of image slices into the x-y plane of the subject.

7. The method of claim 1, wherein the spectrally selective fat suppression pulse is a 180 degree RF pulse which completely inverts longitudinal magnetization of fat in the plurality of image slices and wherein the method further comprises:

waiting a predetermined inversion time prior to performing the simultaneous multi-slice acquisition of the plurality of image slices, wherein the predetermined inversion time is selected such that longitudinal magnetization of fat in the plurality of image slices recovers through a zero point when acquiring k-space data during the simultaneous multi-slice acquisition.

8. The method of claim 1, wherein the simultaneous multi-slice acquisition is performed using a single-shot pulse sequence.

9. The method of claim 8, wherein the single-shot pulse sequence is a balanced steady-state free precession pulse sequence or spoiled gradient echo sequence.

10. The method of claim 1, wherein the acquisition process applies all of the volume-selective venous suppression pulses prior to applying the slice-selective background suppression pulses.

* * * * *